United States Patent [19]

Woodroof

[11] Patent Number: 4,725,279
[45] Date of Patent: Feb. 16, 1988

[54] BIO COMPATIBLE AND BLOOD COMPATIBLE MATERIALS AND METHODS

[75] Inventor: E. Aubrey Woodroof, Fountain Valley, Calif.

[73] Assignee: Sterling Drug Inc., New York, N.Y.

[21] Appl. No.: 738,282

[22] Filed: May 28, 1985

Related U.S. Application Data

[63] Continuation-in-part of Ser. No. 005,319, Jan. 22, 1979, abandoned.

[51] Int. Cl.$^4$ .......................... A61F 2/10; A61F 13/00; A61L 15/00
[52] U.S. Cl. .......................................... 623/15; 623/66; 128/156; 128/157; 128/DIG. 8; 424/DIG. 13; 424/447; 424/448; 427/2; 523/111; 523/112; 523/113; 514/801
[58] Field of Search ............... 623/11, 15, 66; 424/16, 424/27, 28, 32, DIG. 13; 128/157, 156, 165, 155, 160, DIG. 8; 427/2; 435/178; 523/103, 111, 112, 113

[56] References Cited

U.S. PATENT DOCUMENTS

| | | | |
|---|---|---|---|
| 2,693,438 | 11/1954 | Ward | 128/155 |
| 3,457,098 | 7/1969 | Leininger | 623/11 |
| 3,639,141 | 2/1972 | Dyck | 623/11 |
| 3,846,353 | 11/1974 | Grotta | 623/11 |
| 4,001,583 | 1/1977 | Barrett | 424/12 |
| 4,034,751 | 7/1977 | Hung | 128/156 |
| 4,060,081 | 11/1977 | Yannas | 623/15 |
| 4,360,972 | 11/1982 | Montgomery | 128/156 |

FOREIGN PATENT DOCUMENTS

106439  4/1984  European Pat. Off. ............ 128/156

OTHER PUBLICATIONS

Hall et al., "Artificial Skin", Trans. Amer. Soc. Artif. Inl. Organs; 1966; vol. XII pp. 340–343.

*Primary Examiner*—Richard J. Apley
*Assistant Examiner*—Alan W. Cannon
*Attorney, Agent, or Firm*—Beehler, Pavitt, Siegemund, Jagger, Martella & Dawes

[57] ABSTRACT

Bio-and blood compatible materials are prepared by treating the surface of a substrate to provide reactive primary or secondary amine groups sites which are activated by treatment with a dialdehyde or arylchloride for coupling to a biological in an amount sufficient to provide compatibility. The use of specific substrates, such as a compliant, and elastic material, such as a fabric-elastomer membrane matrix, results in a product having advantageous qualities as a thermal burn dressing. Detailed procedures and various products are described including gloves and sleeves and tubes with or without adhesive to facilitate formation of sheet materials into various forms and products. The products may have small holes provided therein for the rapid passage of accumulated fluid away from the wound or infusion of liquid materials to the wound site.

32 Claims, 8 Drawing Figures

BIO COMPATIBLE AND BLOOD COMPATIBLE MATERIALS AND METHODS

BACKGROUND OF THE INVENTION

This application is a continuation-in-part of Ser. No. 005,319 filed 1/22/79, now abandoned.

This invention relates to biocompatible and blood-compatible materials and their method of preparation and more particularly to an improved biocompatible and compliant material of the type described which may be topically or internally applied or contacted by biologicals, blood, or tissue as for example a burn dressing, a surgical dressing, a cardiovascular graft or implant material, and the like, and to the method of making the same.

there are many instances in medicine in which there is need for a bio-and blood compatible material for human and animal use and for use in equipment contacted by biologicals or blood, e.g. tubing, containers, valves, etc. For example, in extracorporial circulation of blood, i.e. heart lung, artificial kidney, there is a tendency for blood to coagulate on contact with a "foreign surface", see for Example U.S. Pat. Nos. 3,643,123 and 3,810,781. Also, products such as heart valves, materials used in coronary and vascular grafts, and catheters, oxygenator tubing and connectors tend to cause thrombosis of blood.

In addition to the above, materials used as burn dressings and surgical dressings should be bio-and blood compatible. In the case of such dressings, an area in which the present invention finds particular utility, there are additional requirements because of the use of the materials.

As is known in the art, and described in U.S. Pat. No. 3,800,792, treatment of second and third degree burns involves a number of phases, including cleaning and stabilizing the wound area to the development of a granulation bed at the wound site. The final phase of treatment is usually the autografting phase which sometimes takes place some period of time after development of the granulation bed. The maintenance of the granulation bed is a necessity until such time as autograft is available and successful autografting is completed.

Several different approaches have been used to preserve the wound site, i.e. granulation bed, for example, application of wet dressings which must be changed frequently and tend to add to patient discomfort. Homografts, heterografts and synthetic dressings have also been used.

Accordingly, a wide variety of dressings, characterized as biological and synthetic, have been used in the treatment of burn wounds. Biological dressings include any dressing that has one or more biological components, i.e. protein, carbohydrates, lipids and the like. Presently, homograft and porcine xenograft skin are dressings currently used to maintain the granulation bed.

In burn patients with large areas of burn tissue, the amount of available skin (autograft) is limited and temporary dressings are required for long periods of time to maintain the granulation bed. Homografts (cadevar skin) is the current dressing of choice, when available. Unfortunately, homograft skin has a limited shelf life and is relatively expensive i.e. $85.00 to $95.00 per square foot. Human amniotic membrane has also been used but is less desirable than cadevar skin. Lack of availability and short shelf life are also drawbacks.

Xenograft (porcine) skin is commercially available but is considerably less effective than homografts or autografts. Short shelf like, sterility and limited application are known disadvantages of this material, in addition to an antigenicity problem.

DESCRIPTION OF THE PRIOR ART

In addition to the materials previously mentioned, various forms of collagen have been used in the treatment of burns, see U.S. Pat. No. 3,491,760 which describes a "skin" made from two different tanned collagen gel layers.

U.S. Pat. No. 3,471,958 describes a surgical dressing made up of a mat of freeze dried microcrystalline collagen, while British Pat. No. 1,195,062 describes the use of microcrystalline colloidal dispersions and gels of collagen to product films which are then applied to various fibers such as polyurethane.

A "biolization" process for improving the blood and biocompatibility of prosthetic devices has been described by Kambic, et al. and others, see Trans. Third Annual Meeting Society for Biomaterials, Vol. 1, p. 42, 1977. Their methods involve deposition of gelatin into a rough textured rubber with subsequent cross-linking and stabilization of the gelatin with 0.45% gluteraldelyde.

Also of interest in U.S. Pat. No. 2,202,566 which describes collagen fibers in bandages and U.S. Pat. No. 3,113,568 which discloses the use of polyurethane foam in a bandage.

There are numerous references in the literature to various othe materials used in burn treatment. For example, collagen membranes have been fabricated from suspensions of bovine skin and evaluated in a rat animal model. The adherence of this material was superior to auto- homo- and xenografts on full and split thickness wounds but inferior to auto- and homografts on granulating wounds, see Tavis et. al., J. Biomed. Mater. Res. 9, 285 (1975) and Travis et. al., Surg. Forum 25, 39 (1974).

McKnight et. al., developed a laminate of collagen foam with a thin polyurethane sheet, see U.S. Pat. No. 3,800,792. Film prepared from reconstituted collagen has also been used, Tavis et. al., supra, and a commercial grade of such material is available from Tec-Pak Inc. Gourlay et. al., Trans, Amer, Soc, Art, Int. Organs 21, 28 (1975) have reported the use of a silicone collagen composition, collagen sponge, and non-woven fiber mats.

Park, "Burn Wound Coverings—A review", Biomat, Med. Dev. Art. Org. 6(1), 1–35 (1978) contains a review, with extensive literature citations, of various burn wound coverings, including laminates of velour fabrics such as nylon, dacron (polyester), rayon, Teflon and polypropylene. Velour silastic laminate are reported with the observation that Teflon and polypropylene velours could be easily peeled off the granulation bed. Rayon appeared to adhere well but disappeared after 10 to 14 days leaving only the silastic backing. Dacron and nylon appeared to adhere well.

Nylon velour incorporating polypeptide films and polycaprolactone films were critized because of cracking of the film. Ultra thin silicone fabric composite membranes have been reported by Kornberg et al., Trans. Amer. Soc. Artif. Int. Organs, Vol. 18, pp. 39–44, 1972.

In the literature reports of some of the above materials, adherence, continued elasticity and flexibility, and water vapor transmission appeared to emerge as important parameters in burn dressings. Thus, as far as burn wound coverings the following characteristics emerge as desirable:
1. The material must adhere to the wound base (comparable to auto- and homograft) to minimize infection and sepsis.
2. It must have adequate flexibility over a period of time in order to cover joints and other areas of body flexion.
3. It must have the proper moisture vapor transmission rate to maintain proper moisture balance at the wound site.
4. It should be capable of being easily stored, sterilized and available for use on short notice for emergency procedures.
5. It must not be toxic, pyrogenic, or antigenic.
6. It should be readily available at reasonable cost.
7. It must be capable of being applied to the wound site so as to completely isolate the site.
8. It must have sufficient strength to be secured by sutures, clips and the like.

In addition to the above, U.S. Pat. No. 3,846,353 describes the processing of silicone rubber with a primary or secondary amine, see also Canadian Pat. No. 774,529.

In addition to the above, there is considerable literature relating to the use of silicone rubber membranes Medical Instrumentation, Vol. 7, No. 4,268,275 September-October 1973; fabric reinforced silicone membranes, Medical Instrumentation, Vol. 9, No. 3,124–128, May–June 1975. U.S. Pat. No. 3,267,727 also describes the formation of ultra thin polymer membranes.

It is also known that various materials may be heparinized in order to impart a non-thrombogenic character to the surface of a material, see for example U.S. Pat. Nos. 3,634,123; 3,810,781; 3,826,678; and 3,846,353, and Canadian Pat. No. 774,529, supra.

SUMMARY OF THE INVENTION

The product and process of the present invention differ from the prior art by providing a composite elastomeric material from a thin film of the thermoplastic (e.g. silicone rubber) and a knitted or woven fabric (e.g. nylon). the thermoplastic component can be layered with high precision (final cured sample thicknessess with a tolerance of ±0.00025 inches). The fabric component is placed on the wet thermoplastic component (without wrinkles) and the composite is cured at a temperature of approximately 300° F. for 15–60 minutes. To this composite elastomeric matrix one or more biological molecules such as proteins (collagen, gelatin, fibrinogen, egg albumin, human albumin, human gamma globulin, or other animal or plant proteins), carbohydrates (acidic mucopolysaccharides, starch, simple sugars, etc.), lipids (lecithin, cloline, unsaturated or saturated free fatty acids, other complex or simple lipids), amino acids (aspartic acid, lysine, glycine; serine, etc.), dipeptides (Glycylglycine, others), larger peptides and the like may be bonded using a number of commercially available reagents to accomplish either hydrophobic or covalent bonds. The process can be thought of as a final product of composition A,B,C,. The "A" represents the elastomeric fabric-thermoplastic composite matrix, which provides ideal physical properties (e.g. elasticity, comformability and water vapor tansport properties).

The "B" represents one or more components used to bond the "C" component (one or more biologicals) to the "A" component (fabric-thermoplastic composite matrix). The completed product A-B-C is used to impart a specific quality or a combination of characteristics of the material (A-B-C) to render them bio-and blood compatible.

The materials of the present invention also exhibit a moisture vapor transmission rate, i.e. the weight of water lost by evaporation through a film membrane at 37° C. over a period of 24 hours, of about 10–15 grams per hour per meter squared or about 1–1.5 miligrams per hour per centimeter squared, which is a rate similar to human skin, however, the WVT property of these materials are subject to modification to optimize wound healing.

Where used as a burn dressing, which is the principal but not the sole use of the materials of this invention, the material exhibits a moisture vapor transmission rate in the range indicated and, because of the inclusion of biological components, exhibit good adherence to the burn area. Thus, the materials of the present invention, used as a burn dressing preferably is in the form of a laminate including a thin film of thermoplastic polymer, e.g., silastic rubber, urethane or other elastomeric polymer material, the film of polymer being of such dimensions and composition as to have a water vapor transmission rate in the range indicated. Physically bonded to the thin polymer film is a thin porous fabric such that the composite is elastic in all directions, i.e. length and width. Covalently coupled to one or both sides of the laminate is one or more biological materials to provide adherence and compatibility to the wound site.

Ragardless of the form of the substrate, sheet, tube, formed contour and the like, the biological compound is bound by treating the substrate with a primary or secondary amine such that the amino groups are available for further reaction. In one form this is accomplished by incorporating the primary of secondary amine into the substrate such that the amino functional groups extend out of the surface as coupling sites. In another form, the substrate is coated with a primary or secondary amine silating agent in order to provide terminal available amino functional groups, again as coupling sites.

The first form above described is similar in part to the procedure described in U.S. Pat. No. 3,634,123 and the primary and secondary amines there disclosed may be used in this form of the present invention.

the second form above described offers the advantage of being able to provide available amino groups reactive sites with a variety of substrates both of organic and inorganic character, i.e. substrates other than silastic, urethane, for example other plastics to which the material will adhere to, or to inorganics such as metal or glass.

The procedures thus far described are distinguishable from those of U.S. Pat. No. 3,846,353 which use a long chain alkyl quaternary ammonium salt to ionicly bind heparin to various polymer substrates.

According to the present invention, the available amino functional groups are then activated for bonding to a biological. This is in contrast to U.S. Pat. No. 3,634,123 in which heparin is ionicly linked to the positively charged amine directly, or in contrast to U.S. Pat. No. 3,810,781 which treats the substrate-amine hydrochloride-heparin salt subsequently with a dialdehyde, such as glutaraldehyde, to stabilize the heparin on the substrate surface.

Activation of hte amino groups, according to the present invention may be accomplished by one of several ways. In one form dialdehyde, such as glutaraldehyde, is reacted with the primary or secondary amine provided by either of the procedures described, leaving available aldehyde groups average of one per molecule of glutaraldehyde for subsequent reaction with the primary or secondary amines of either proteins, mucopolysaccharides or other amine containing biologicals. In another form, the preferred form, cyanuric chloride is reacted with the primary and secondary amines provided on the substrate as previously described. The available chloride groups of cyanuric chloride may then be used to react with the primary or secondary amines or hydroxyl groups of various biologicals to form covalent bonds.

Other bifunctional reagents that may be used to link substrate amines with biological amines are thiophosgenes, isocyanates, derivatized cynauric chloride (one Cl group removed or alkylated), 1,5-difluoro-2,4-dinitrobenzene, diazobenzidine, toluene-2,4-diisothiocyanate and others.

Thus, a wide variety of new, improved and relatively simple procedures are described for attaching various biologicals on a substrate which, in accordance with this invention, may be used as burn covering having the desirable properties mentioned.

One of the qualities of the products above described is that the composite is stretchable, and preferably biaxially stretchable, as will be described in detail. This quality of the products of this invention is of significance in that it allows the formation of products of various configurations for use in the treatment of burns. For example, through the use of adhesive path type elements or other suitable adhesives, the sheet material may be applied to the skin surface and immobilized in place on the wound by adherence of the adhesive to the skin, thus eliminating the use of sutures, staples and the like. Placement of adhesive strips and sewing also allows the formation of stretchable tubes and glove-like elements for treatment of neck, trunk, finger, toe, arm, and leg burns in the case of tubes, and hand burns in the case of gloves. Hand burns may present problems in treatment, especially if there are burn areas between the fingers and where the fingers join the palm. the stretchability of the product of the present invention is thus of significant practical utility in assuring that there is good skin contact as well as stretchability to permit reasonable range of natural movement of the body member affected. The ability to permit reasonable range of movement tends to minimize rehabilitation complications. Good skin contact tends to promote acute adherence, which is further enhanced by the biological coating, in that good acute adherence is desirable in burn therapy.

It will be apparent from the following detailed description and specific examples and data that a much improved bio- and blood compatible material has been provided by a relatively simple and reliable procedure. the further advantages and features may be understood with reference to the following description of the invention.

DETAILED DESCRIPTION OF THE INVENTION

The present invention relates to bio-and blood compatible materials which may take various forms and shapes. for example, rigid and flexible tubes, sheets or formed and contoured shapes, for use in equipment and or in patients. Since burn wound coverings, one form of the present invention, include the characteristics of adhesion to the wound site and elasticity in all directions, although it will be understood by those skilled in the art that the present invention is not limited to such dressings, but has applicability to bio- and blood compatible materials.

In general, the present invention relates to a novel and improved bio- and blood compatible material in which specific characteristics are imparted to a substrate by a novel, simple, effective and inexpensive procedure for covalently coupling to the substrate certain biological materials or combinations thereof. Typical of the biological materials which can be covalently coupled to the substrate are those which include an available primary or secondary amine reactive group which can react with an aldehyde group or arylchloride group (i.e. or cyanuric chloride or its derivative) and those which include an available hydroxyl group which can react with an arylchloride group. Representative materials are proteins, collagen, albumin, gelatin, fibrinogen, animal or plant proteins, complex carbohydrates (i.e.: acidic mucopolysaccharides) simple carbohydrates, lipids, (i.e.: lecithin), peptides and amino acids. Typical of the complex carbohydrates are heparin, hyaluronic acid, chondroitin sulfate A and C, to mention only a few.

Conceptually the improved and novel products of the present invention, produced by the improved and novel process of this invention, include a suitable substrate treated to provide available and reactive primary or secondary amine functional reactive sites. The amine functional sites are then activated either by reaction with a dialdehyde, or preferably cyanuric chloride to provide available active aldehyde or arylchloride groups, respectively. Thereafter, one or more biological materials, as previously described, having a hydroxyl, primary or secondary amine, is then coupled to the available free aldehyde or arylchloride group. In this way select biologicals are covalently coupled to the substrate in an amount and in a form sufficiently stable to provide bio- and blood compatibility to the substrate.

The useable substrates may be a wide variety of materials depending upon the procedure and to provide available primary and secondary amine functional reactive sites. For example, a reactive silicone containing a primary or secondary amine may be used as a primer and coated on the substrate to provide the reactive amine group. Such a procedure is described in Canadian Pat. No. 774,529, however, the amine is then alkylated to form a positively charged quaternary ammonium salt which is then used to ionicly bind heparin to the surface of the substrate.

Thus, typical substrates are glass, and the elastomers, silicone rubbers and thermoplastics used in medical applications. Representatives of such materials are:

silicone rubbers and elastomer polysiloxanes, natural rubber, polybutadiene, styrene-butadiene, butyl rubber, for example;

thermoplastics such as polyethylene, polypropylene polystyrene, polyvinylchloride, polyvinyl acetate, ethacrylate and methacrylate polymers and copolymers and the like.

For burn wound dressings it is preferred to use silicone rubbers of membrane thickness as will be described.

A useable primer is an aminofunctional silane coupling agent such as gamma (Beta-aminoethyl) aminopropyltrimethoxysilane, available as Dow Corning Z-6020. This primer also bonds well to materials such as nylon, dacron and the like, the latter may optionally be components of the substrate, as will be apparent with the description of burn wound dressings.

A typical aminofunctional silating primer and its application are as follows:

Four milliliters of the aminofunctional silating agent was added to 4 milliliters of absolute methyl alcohol along with 0.32 milliliters of distilled water and the resultant material was allowed to sit overnight at room temperature. To the primer solution 69 milliliters of absolute methyl alcohol was added to make a dipping solution into which silicone rubber membranes were dipped for 3-5 seconds. The membranes were then dried in an oven at 100°-110° C. for 40 to 60 minutes. The result is a substrate having primary amino functional groups thereon for further reaction as will be described.

Primary or secondary amine functional groups may also be attached to a substrate by physically entrapping an alkyl amine in the substrate (i.e. dodecylamine or other organic primary or secondary amines). For example, using a silicone rubber, a solvent in which the amine will dissolve and which causes the rubber to swell, a substrate may be formed with amine functional groups trapped therein and thereon. In a typical example, 4% by volume of dodecylamine (by volume) was dissolved in a 60:40 solvent mixture of toluene and isopropyl alcohol. The substrate was immersed in the amine solution, at room temperature, for 5-8 seconds and then allowed to dry at room temperature for an additional 10-20 minutes. The result is a substrate wherein primary or secondary amine functional groups are attached and available for further reaction.

In the case of burn wound dressings, which represents a preferred form of this invention, the substrate preferably is in the form of a thin rubber membrane-fabric composition which is stretchable in all directions and which has a water vapor transmission rate of between 6 to 12 grams per hour per meter square foot. Also, the burn covering substrate should be sufficiently strong so that in normal handling and use it does not tear.

A typical burn covering substrate material may be prepared as follows:

A dispersion of 13% dimethylsiloxane elastomer is layered with a precision layering tool at a uniform thickness of 0.006, 0.008, 0.010, 0.012, 0.014, 0.016, 0.018 or 0.020 inches thick plus or minus 0.0003 inches over a mylar (polyethylene terephtalate) support member. A typical silicone rubber which may be used is that available from Dow Corning as Q7-2213. After deposition of the dispersion, a firmly knitted fabric (dacron or nylon), or 25 denier or less is laid over the wet silicone rubber. For example, a 12 denier monofilament fabric of nylon or dacron or an 18 denier triple filament nylon or dacron material may be used. The fabric is preferably one which is stretchable to 100% or more elongation in all directions. The uncovered composite is allowed to sit at room temperature for 15 minutes and then transferred and cured in an oven at 150° C. for about one hour. The cured composites, still on the support is then stored until processing for binding biologicals thereto.

After curing, the thickness of the silicone rubber is 0.0006, 0.0008, 0.00010, 0.0012, 0.0014, 0.0016, 0.0018 or 0.0020 inches plus or minus 0.0003 inches. Thickness of 0.0008, 0.0010 and 0.0012 inches are preferred for burn dressing membranes. Prior to chemical modification the cured composite may be removed from the mylar support, without the use of release agents, by immersing the support and composite in a 60:40 toluene and isopropyl alcohol solution for 10 minutes at room temperature. The composite is gently pulled off the support and allowed to air dry prior to modification.

The above described composite is a substrate, stretchable in all directions, and having a water vapor transport rate in the range noted and adaptable to modification. The fabric is located at the face of one side of the membrane, i.e. partly imbedded in the membrane with portions of the fabric exposed. In use, the fabric side is applied over the woundside so that the fabric faces the wound.

Attachment of biologicals to the burn dressing involves first attachment of primary or secondary amine groups on one or both sides of the composite. This may be done by either of the procedures already described. Regardless of the procedure, it is noted that amine groups are present on the exposed fabric surface side as well as on the exposed membrane surface side.

The next setep in accordance with this invention, regardless of the nature of the substrate, is to activate the amine functional groups. The preferred procedure in accordance with this invention is as follows:

A saturated solution of cyanuric chloride in acetone is prepared and chilled to 0° C. The substrate (silicone rubber-fabric composite with attached amine functional groups) is then immersed in the chilled solution for 10 seconds. As a result, a bond through the amine to cyanuric chloride at the site or one of the chlorides is formed so that there is now available two chloride groups on the cyanuric chloride available for further reaction.

While the use of cyanuric chloride is preferred because it is more reactive, it is also possible to activate the amine functional groups by reaction with a dialdehyde, such as glutardialdehyde. U.S. Pat. No. 3,810,781 described the use of this material to stabilize heparin ionicly bound to a substrate containing a positively charged amine, i.e. the heparinized surface is subsequently treated with the dialdehyde. In contrast, the present invention reacts the amine with the dialdehyde to provide a reactive aldehyde group covalently bound to amine-substrate surface.

Thus, a typical procedure involves incubating a substrate with the primary or secondary amine thereon, formed as described by either of the previous procedures, in a 0.5% solution of glutaraldehyde solution, 1/15 M disodium hydrogen phosphate, pH 8.2-8.3 for 2-3 hours at room temperature. The result is a substrate in which the primary or secondary amine has reacted with one of the aldehyde groups of glutaraldehyde to form a Schiff Base covalent bond leaving the other primary or secondary amine containing compounds.

Linkage of the biological may be accomplished one of several ways, depending upon the nature of the biological and the type of amine activation. For example, in the case of proteins, a 0.5-2.0% solution of the protein in 1/15 M disodium hydrogen phosphate solution is prepared, pH 8.2-8.3 and the activated substrate is taken directly from the glutaraldehyde activating solution submerged and incubated in the protein solution for 2-8 hours at 25°-55° C. The amine-silicone-fabric composite material can also be activated by cyanuric chloride and biologicals bound by being taken from the saturated cyanuric chloride solution and incubated in a protein solution as described. Essentially the same procedure is used for attachment of mucopolysaccharides to the substrate surface (e.g.: a 0.5% buffered solution thereof as described, and incubated as described).

Depending upon the route taken the biological is covalently bounded through the primary or secondary amine groups of the biological, through the aldehyde to the amine to the substrate. In the case of cyanuric chloride activation, the primary or secondary amine or hydroxyl groups of the biological is covalently coupled through the cyanuric chloride to the amine to the substrate.

By way of illustration of the products of the present invention and the unique character of the biologically activated materials which are bio- and blood compatible, various products were prepared and evaluated as burn dressings in terms of adhesion to animals. The test involved removing the skin of the test animal (rats) and testing the adherence of various products to the subdermal facial tissue. Circular test coupons of 6 mm in diameter were prepared from each material type and the discs were applied at ten different locations on each of the test animals. After 5 hours, the force in grams necessary to remove each of the disc was measured by a tensiometer and adherence was recorded in grams/cm$^2$. The test was repeated for a 72 hour adhesion period and the data again collected. (Details of the test methodology is described by Tavis et al., Annuals of Surgery, Vol. 184, No. 5 pg. 594-600, 1976).

As a basis for comparison, products of the present invention were compared with homograft, pigskin and modified bovine collagen membrane, the material with the highest adherence was assigned a value of 100 and other materials were normalized on the basis of their adherence value. All samples were ranked in overall adherence both at 5 hours and 72 hours. The following codes were used to describe each of the products of this invention and the materials evaluated for adherence.

The material code is a series of three letters, x x x, the first letter describing the substrate; the second letter, the activating agents/bonding agent(s); and the third, the biological component bonded to the surface.

The activating agent(s)/bonding agent(s) code is as follows:
A. Dodecyl amine, glutaraldehyde treatment of amine.
B. Silated by coating, glutaraldehyde treatment of amine.
C. Dodecyl amine, cyanuric chloride activation.
D. Silated by coating, cyanuric chloride activation.
E. Dodecyl amine.
F. Silated by coating.
G. No activating agents.

The substrate (fabric silicone rubber composite) code is as follows:
A. Edwards membrane-cotton gauze/silicone rubber (see infra).
B. 18/3 nylon fabric 300%×50% elongation.
C. 18/3 nylon fabric 150%×240% elongation.
D. Silicone rubber without fabric.

The code for the biological component bonded to the activated surface, is as follows:
A. Heparin
B. Chondroitin sulfate C
C. Egg albumin
D. Collagen (tropocollagen-rat skin)
E. Lysine
F. Fibrinogen
G. Hemogoblin
H. Aspartic Acid
I. Alanine
J. Glutamic Acid
K. Glycine
L. Glyclglycine
M. Human albumin
N. Gelatin (Porcine Skin)
O. Nothing
P. Lecithin Overall, the test involved evaluation of a multiplicity of materials, including those presently in use, for the purpose of establishing adherence of the products of the present invention for use as burn dressings. Those materials such as the Edward Membrane formerly made by Edwards Laboratories A Division of Amer. Hosp. Supply Corp. and Pigskin, homograft and Collagen membrane formerly made by Edwards Laboratories offer a basis for comparing the adherence of the products of this invention with those recognized in the field as being of use as burn dressings. The Edwards membranes is a composite of a silicone rubber polymer backing and a non-elastic cotton gauze facing and having a substantial thickness variation (0.0005-0.0020 inches thick) as compared to the thin membrane material substrates of the present invention. Further the Edwards membrane is not as stretchable as the substrates of the present invention, the latter preferable having greater than 100% elongation in all directions. Moreover, the Edwards membrane is not biologically activated, although as a basis of comparison, this membrane was used as a substrate and activated in accordance with this invention. Collagen membrane has a cotton gauze component, the same as the Edwards material.

In the test, with the exception of homograft and pigskin, which do not include fabric, all substrates were applied with the fabric side in contact with the dorsal facial surface of the test animal. The circular coupons were applied principally to the backs of the test rats to prevent them from being reached and possibly eaten by the test animals. In some instances the patches were scraped loose when the animals contacted the cage walls in their normal movements in the cages. Where this occurred, a value of zero was used and totaled and averaged in the data.

TABLE I

ADHERENCE DATA SUMMARY
5 hr. Adherence Test

| Rank | Sample # | Material | Adherence (gm/cm$^2$) | % Maximum Adherence | # Adhering of 10 Samples Placed |
|---|---|---|---|---|---|
| 1 | 25 | Homograft | 167 | 100 | 8 |
| 2 | 23 | Collagen M. | 133 | 80 | 7 |
| 3 | 24 | Pigskin | 116 | 69 | 9 |
| 4 | 2 | ACC | 99 | 59 | 9 |
| 5 | 19 | BDC | 95 | 57 | 6 |
| 6 | 14 | ADK | 86 | 51 | 8 |
| 7 | 1 | ADC | 82 | 49 | 8 |
| 8 | 13 | ADE | 68 | 41 | 9 |
| 9 | 11 | ADD | 63 | 38 | 9 |
| 10 | 8 | ACK | 59 | 35 | 9 |
| 11 | 18 | BCC | 54 | 32 | 6 |
| 12 | 9 | ACG | 52 | 31 | 9 |
| 13 | 12 | ADB | 51 | 31 | 8 |
| 14 | 17 | ABC | 49 | 29 | 7 |
| 15 | 10 | ADR | 49 | 29 | 8 |
| 16 | 20 | BCD | 47 | 28 | 7 |
| 17 | 15 | ADG | 44 | 26 | 9 |
| 18 | 22 | BDC$_2$ | 44 | 26 | 9 |
| 19 | 21 | DBB | 42 | 25 | 8 |
| 20 | 16 | AAC | 31 | 19 | 6 |
| 21 | 5 | ACD | 30 | 18 | 9 |
| 22 | 4 | ACF | 30 | 18 | 10 |
| 23 | 3 | ADC | 28 | 17 | 9 |
| 24 | 7 | ACE | 26 | 16 | 8 |
| 25 | 6 | ACB | 22 | 13 | 9 |
| MEAN ± STD. DEV. | | | 62.7 ± 36 | 28 ± 25 | 8.2 ± 1.1 |

TABLE II

ADHERENCE DATA SUMMARY
72 hr. Adherence Test

| Rank | Sample # | Material | Adherence (gm/cm$^2$) | % Maximum Adherence | # Adhering of 16 Samples Placed |
|---|---|---|---|---|---|
| 1 | 13 | ADE | 524 | 100 | 10 |
| 2 | 25 | Homograft | 512 | 98 | 6 |
| 3 | 14 | ADK | 499 | 95 | 10 |
| 4 | 6 | ACB | 498 | 95 | 11 |
| 5 | 17 | ABC | 483 | 92 | 11 |
| 6 | 23 | Collagen M. | 472 | 90 | 6 |
| 7 | 12 | ADB | 457 | 87 | 10 |
| 8 | 15 | ADG | 455 | 87 | 8 |
| 9 | 18 | BCC | 455 | 87 | 14 |
| 10 | 20 | BCD | 499 | 86 | 13 |
| 11 | 16 | AAC | 435 | 83 | 10 |
| 12 | 24 | Pigskin | 424 | 81 | 5 |
| 13 | 3 | ADC | 420 | 80 | 9 |
| 14 | 5 | ACD | 419 | 80 | 10 |
| 15 | 2 | ACC | 399 | 76 | 12 |
| 16 | 21 | BDD | 395 | 75 | 6 |
| 17 | 11 | ADD | 392 | 75 | 13 |
| 18 | 9 | ACG | 379 | 72 | 10 |
| 19 | 10 | ADF | 372 | 71 | 11 |
| 20 | 8 | ACK | 339 | 65 | 10 |
| 21 | 19 | BDC | 335 | 64 | 12 |
| 22 | 1 | ADC$_2$ | 328 | 61 | 10 |
| 23 | 22 | BDC$_2$ | 272 | 52 | 9 |
| 24 | 7 | ACE | 246 | 47 | 8 |
| 25 | 4 | ACF | 244 | 47 | 6 |
| MEAN ± STD. DEV. | | | 408 ± 79 | 78 ± 15 | 9.6 ± 2.4 |

TABLE III

ADHERENCE DATA SUMMARY
5 hr. Adherence Test

| Rank | Sample # | Material | Adherence (gm/cm$^2$) | % Maximum Adherence | # Adhering of 10 Samples Placed |
|---|---|---|---|---|---|
| 1 | 22 | BDH | 389 | 100 | 9 |
| 2 | 24 | Collagen M. | 378 | 97 | 10 |
| 3 | 16 | BDK | 297 | 76 | 10 |
| 4 | 6 | BDO | 287 | 74 | 8 |

TABLE III-continued
ADHERENCE DATA SUMMARY
5 hr. Adherence Test

| Rank | Sample # | Material | Adherence (gm/cm²) | % Maximum Adherence | # Adhering of 10 Samples Placed |
|---|---|---|---|---|---|
| 5 | 10 | BDF | 283 | 73 | 8 |
| 6 | 25 | Homograft | 269 | 69 | 10 |
| 7 | 13 | BCM | 261 | 67 | 10 |
| 8 | 21 | BCH | 244 | 63 | 10 |
| 9 | 4 | BFO | 230 | 59 | 9 |
| 10 | 18 | BDL | 230 | 59 | 10 |
| 11 | 17 | BCL | 216 | 56 | 9 |
| 12 | 2 | AOO | 191 | 49 | 9 |
| 13 | 12 | BDC | 180 | 46 | 10 |
| 14 | 3 | BEO | 177 | 46 | 2 |
| 15 | 19 | BCE | 177 | 46 | 10 |
| 16 | 1 | BOO | 173 | 44 | 9 |
| 17 | 14 | BDM | 163 | 42 | 10 |
| 18 | 5 | BCO | 158 | 41 | 10 |
| 19 | 9 | BCF | 149 | 38 | 7 |
| 20 | 15 | BCK | 145 | 37 | 10 |
| 21 | 20 | BDE | 145 | 37 | 10 |
| 22 | 11 | BCC | 134 | 34 | 10 |
| 23 | 7 | BCD | 120 | 31 | 9 |
| 24 | 8 | BDD | 113 | 29 | 10 |
| 25 | 23 | Pigskin | 85 | 22 | 8 |
| MEAN ± STD. DEV. | | | 208 ± 78 | 53 ± 20 | 9 ± 2 |

TABLE IV
ADHERENCE DATA SUMMARY
72 hr. Adherence Test

| Rank | Sample # | Material | Adherence (gm/cm²) | % Maximum Adherence | # Adhering of 16 Placed Samples |
|---|---|---|---|---|---|
| 1 | 4 | BFO | 601 | 100 | 8 |
| 2 | 9 | BCF | 584 | 97 | 2 |
| 3 | 6 | BDO | 548 | 91 | 7 |
| 4 | 18 | BDL | 527 | 88 | 3 |
| 5 | 19 | BCE | 520 | 87 | 11 |
| 6 | 15 | BCK | 509 | 85 | 6 |
| 7 | 13 | BCM | 502 | 84 | 10 |
| 8 | 21 | BCH | 495 | 82 | 11 |
| 9 | 5 | BCO | 467 | 78 | 7 |
| 10 | 8 | BDD | 463 | 77 | 7 |
| 11 | 7 | BCD | 460 | 77 | 7 |
| 12 | 2 | AOO | 431 | 72 | 5 |
| 13 | 11 | BCC | 431 | 72 | 10 |
| 14 | 24 | Collagen M. | 417 | 69 | 11 |
| 15 | 14 | BDM | 410 | 68 | 9 |
| 16 | 12 | BDC | 389 | 65 | 12 |
| 17 | 10 | BDF | 382 | 64 | 4 |
| 18 | 20 | BDE | 378 | 63 | 11 |
| 19 | 23 | Pigskin | 375 | 62 | 12 |
| 20 | 17 | BCL | 357 | 59 | 5 |
| 21 | 16 | BDK | 347 | 58 | 8 |
| 22 | 25 | Homograft | 336 | 56 | 8 |
| 23 | 1 | BOO | 332 | 55 | 2 |
| 24 | 22 | BDH | 308 | 51 | 8 |
| 25 | 3 | BED | 304 | 51 | 5 |
| MEAN ± STD. DEV. | | | 435 ± 85 | 72 ± 14 | 7.6 ± 3 |

TABLE V

| Material | Number of Animals (Rats) | Average Starting Weight (gms) | Percent Mortality (3 Wks) | Average Weight Gain (gms/day) and Correlation with Time (r) | | Relative Synthetic Skin Performance (Adherence and Conformance/100 max. Value) | | |
|---|---|---|---|---|---|---|---|---|
| | | | | (gms/Day) | (r) | WK-1 | WK-2 | WK-3 |
| BDK | 6 | 298 | 33 | .88 | .65 | 52 | 29 | 23 |
| BFO | 5 | 298 | 20 | −.38 | −.44 | 53 | 20 | 20 |
| BDE | 8 | 290 | 37.5 | 1.0 | .95 | 60 | 35 | 28 |
| BDH | 5 | 298 | 60 | 1.1 | .86 | 54 | 20 | 0 |
| BDC | 6 | 276 | 16.7 | 1.35 | .96 | 61 | 33 | 25 |
| BDL | 6 | 269 | 16.7 | 1.39 | .97 | 60 | 32 | 28 |
| BCC | 7 | 278 | 57 | 1.41 | .82 | 81 | 53 | 50 |
| BCH | 5 | 329 | 0 (2 wks) | 1.85 | .99 | 76 | 45 | No Data |
| MEAN ± | 6 ± 1.1 | 292 ± 18.8 | 30 ± 21 | 1.1 ± .66 | .72 ± .48 | 62 ± 11 | 35 ± 10 | 25 ± 15 |

TABLE V-continued

| Material | Number of Animals (Rats) | Average Starting Weight (gms) | Percent Mortality (3 Wks) | Average Weight Gain (gms/day) and Correlation with Time (r) | | Relative Synthetic Skin Performance (Adherence and Conformance/100 max. Value) | | |
|---|---|---|---|---|---|---|---|---|
| | | | | (gms/Day) | (r) | WK-1 | WK-2 | WK-3 |
| STD. DEV. | | | | | | | | |

The data in Table V represent the results of a test in which the best materials, based on adherence data were placed on 20% full thickness dorsal defects of rats. Evaluations were made each week and values assigned for adherence and conformity, as follows:

| Membrane Adherence | Membrane Conformity |
|---|---|
| 3. No adherence | 1. No observation-non-adherent |
| 2. Minimal | 2. Minimal adherence with ridges and ripples |
| 3. Moderate | 3. Moderately adherent with ridges and ripple |
| 4. Mostly adherent | 4. Mostly adherent with ridges and ripples |
| 5. Very adherent | 5. High conformity and adherence. |

On the basis of the above data and further testing it was found that the bio- and blood compatible materials of the present invention when structured for use as a burn dressing optimally includes a substrate which is substantially stretchable, compliant, and comformable. A preferred material is, accordingly, material C (18/3 nylon fabric 150%×240% elongation) primarily because of the ability of the substrate to stretch and conform to the area of application.

In combination therewith, it is preferred to use a bonding agent such as dodecyl amine which is cyanuric chloride (C) activated with gelatin (porcine skin) coupled thereto. Also useable is a coated silating material (D).

By way of example, a comparison of the preferred burn dressing with the accepted standard demonstrate the performance of the preferred material:

| Material | Performance | No. of Animals |
|---|---|---|
| Pigskin | 87.2 ± 11.4 | 14 |
| CCM | 97.6 ± 4.6 | 12 |
| CDN | 91.2 ± 9.6 | 16 |

The above data are significant in establishing the superiority of these fabricated materials over the others and those naturally available when used as burn dressings. It is to be understood, however, that other combinations of components may be preferred based on other ultimate uses of the materials of this invention.

Although coupling of the biological has been described, under proper conditions other techniques, known in the art may be used, see for example "Immobilized Enzymes For Industrial Reactors", Messing, Academic Press, N.Y. 1975, pages 99-123. The preferred system, however, is that as set forth herein.

The above described materials, especially those of Table V and CCN and CDN represent the better of the group prepared for use as burn dressings, the test data on rats established the ability of the better materials to remain adherent with nearly complete connective tissue in-growth and without suppuration for periods up to one month.

The materials are easily packaged, easily sterilized or other appropriate procedures and possess a relatively long shelf life.

It will also be apparent from the foregoing description that the products are relatively easily fabricated since the effective chemical reactants are easily attached by appropriate chemical bonds to various substrates. Since the reactions are relatively fast and controllable, selected surface portions or all surface portions may be treated to provide one or more zones of various desired biologicals.

Further, preliminary data on several of the specific biologicals indicates that the materials are non-extractable, free of bio- and blood extractable contaminants and non-antigenic.

In the case of burn dressings, an important practiced application of the present invention, the novel substrate in membrane form which is stretchable and compliant and thus easily fits a variety of body contours, offers unique advantages over prior materials. Also, the effective attachment of effective biologicals provides for adherence to the wound site over extended periods, with proper water vapor transport through the membrane, important characteristics in burn therapy for dressings of this type.

As previously indicated, the stretchable nature of the product of the present invention provides the unique ability to form the initially formed sheet into a variety of configurations. In addition, the stretchable nature of the product, while providing a compliant material also allows it to be fashioned into products which may be initially stretched such that in the relaxed state the active surface firmly contacts the skin, or which may contact the skin while in a stretched condition. The initially formed flat sheet may be fashioned into a preformed product or fashioned into the desired configuration immediately prior to use.

Figure 1:
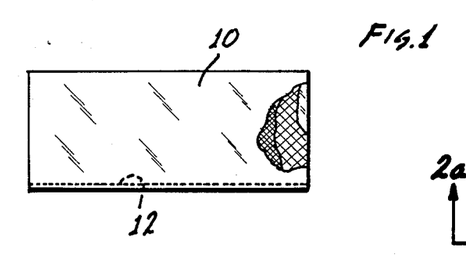
FIG. 1 is a plan view of one form of product in accordance with the present inveniton in the form of a tubular element.

Thus for example, referring to FIG. 1, the member 10 is illustrated in the form of a hollow, elongated and stretchable tubular member made of the sheet material as previously described. In this form, the tube is formed by stitching 12 along one side, such that the member is initially flat. The active surface is the interior surface (fabric side) of the tube, designed to adhere to clean hemostatic wounds, and the tube may be fashioned by folding a rectangular sheet such that the biologically active fabric side is in facing relation, and then stitching as illustrated. After stitching, the product is sterilized, as described and sterily packed in a sterile package. Since the tube is stretchable axially and radially, it may be used for fingers, arms, trunk, legs or any other appendages which are generally cylindrical in shape, such as toes, fingers and the like. Again the stretchable nature of the basic material allows the preformation of tubular products of various dimensions. The tubular member may be proportioned such that when located in place, the tube snugly engages the member on which it is positioned, and the tubular member is in tension radially. Again, the stretchable and compliant nature of the product when coupled with the use of a biological tends to promote acute adherence to the wound site.

Figure 2:
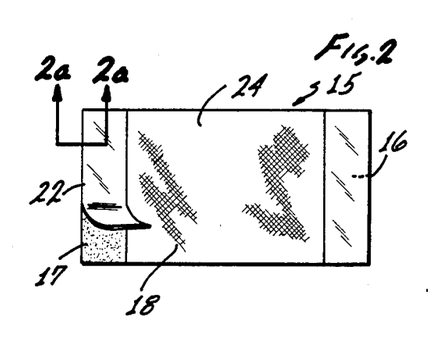
FIG. 2 is a plan view of another form of product in accordance with the present invention which includes adhesive strips along each end or around the perimeter thereof for adherence to the skin or for formation into a tubular member.
Figure 2A:
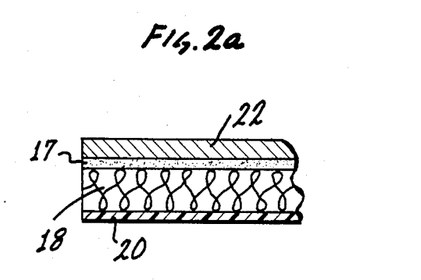
FIG. 2a is an enlarged fragmentary section taken along the line 2a-2a of FIG. 2.

Another form of product in accordance with the present invention is illustrated in FIGS. 2 and 2a in the form of a flat sheet 15 which may be rectangular in shape, as shown, although other geometric shapes may be used. Located along two side edges of the sheet are spaced strips 16, 17 of adhesive. In a preferred form, the adhesive 17 is applied to the fabric side 18 of the composite which includes the thin membrane member 20 to which the stretchable fabric 18 is joined, as previously described. Overlying the adhesive 17 is a liner 22 which is removed to expose the surface of the adhesive strip. A typical material which may be used as the adhesive-liner material is a product available from Minnesota Mining and Manufacturing Co. In general the adhesive-liner product is a double coated microporous nonwoven/tissue transfer medical tape with a hypoallergenic adhesive designed for use on human skin. A preferred material is that available under the designation of Tape Number 1513. This product as initially supplied is a double tacky adhesive strip in which the adhesive is sandwiched between two liners. In manufacture of the product of FIGS. 2 and 2a, the fabric-silicone composite is produced as described with the biological on the fabric side, as discussed. Thereafter, one of the liners is removed from the strip and the remaining adhesive and liner is placed such that the exposed adhesive contacts the fabric to adhere the adhesive to the fabric as illustrated in FIG. 2a. After assembly, the resultant product is sterilized and sterile packed as described.

In use, the liner 22 is removed to expose the adhesive and the sheet may be positioned such that the free surface 24 covers the affected skin area and the exposed adhesive secures the sheet in place. The second adhesive strip (16 or 17) may be used to secure the other edge of the sheet in place to the skin, again by removing the liner 22 and firmly pressing the portion of the sheet bearing the adhesive firmly into contact with the skin. The use of adhesive patches, as described, may eliminate the necessity for the use of sutures or the like as may have been heretofore used to secure the sheet in place. This is particularly beneficial where the product is used while the patient is not anesthesised in that it is virtually painless. The sheet material 15 and the surface 24 are stretchable, as described and include a biological linked thereto as already described. As illustrated, the fabric side of the sheet is placed in contact with the skin.

One of the advantages of the product illustrated in FIGS. 2 and 2a is the fact that the spaced adhesive sections may be used to adhere the sheet to itself, for example, the sheet may be affixed to the arm by one patch of the adhesive. The sheet is then wrapped around the arm, with the second adhesive patch used to adhere the free end of the sheet in place. This particular form of the product of the present invention permits a variety of uses. Thus, the sheet may be cut into small strips, formed into a generally cylindrical shape, and the like. Again, since the sheet is biaxially stretchable, pliant and conformable, it may be set initially to have excellent contact with the affected area.

Figure 3:
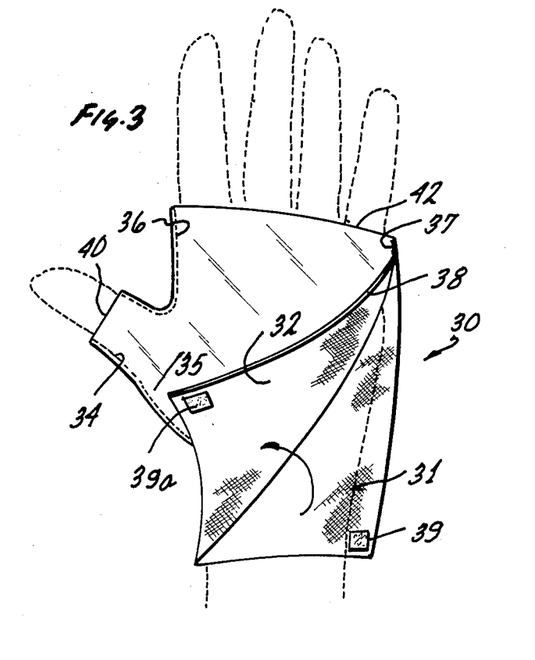
FIG. 3 is a plan view, somewhat in perspective, of a glove-type product in accordance with the present invention.

In hand burns in which the thumb, back of the hand and palm are involved the product illustrated in FIG. 3 may be used. The open glove product 30 includes two sheets of the biaxially stretchable and activated materials already described, which are cut to the general contour of a glove, as shown. The sheets are placed so that the fabric and activated surfaces 31 and 32 are in facing relation and the sheets are joined as by stitching and the like, although other means may be used to join the sheets. The stitching 34 extends along one side 35 which represents the portion of the hand from the wrist to about midway of the thumb. There is further stitching 36 along the portion between the thumb and the joint to the palm and the forefinger. Another short stitched portion 37 is placed along the region where the pinkie joins the palm. The portion from the stitched portion 37 to the rear is unstitched to form a flap 38, for ease of insertion of the hand into the open glove. The inside surface of the flap and the opposed surface of sheet 31 are provided with adhesive patches 39 and 39a, as shown. These patches may be as already described.

In use, the flap 38 is folded back as shown, and the open glove 30 is positioned over the hand with the thumb positioned in the thumb section 40, which is open ended. The fingers extend through the open end 42 which is fingerless. Once properly positioned, the adhesive liners are removed and the flap is positioned such that the patches adhere to each other. If desired, only one patch is used. The advantage of using two patches is that the flap may be stretched to provide a gentle grip, in which case one patch is adhered to the skin and the other to the sheet.

Figure 4:
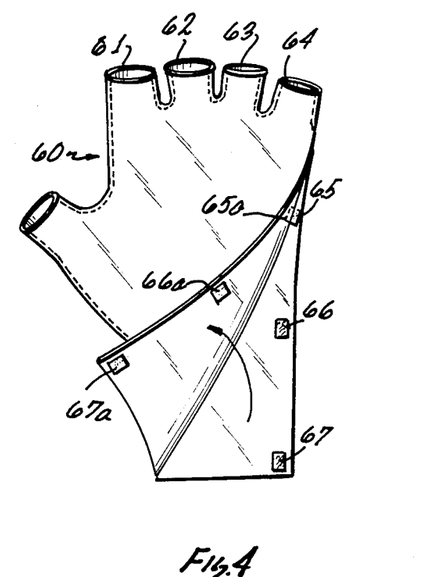
FIG. 4 is a plan view, again somewhat in perspective, of another form of glove-type product in accordance with the present invention.

In cases in which there are burn areas between the fingers, but not along the length of the fingers, the short fingered glove 60 of FIG. 4 may be used. This glove is essentially the same as that illustrated in FIG. 3, but includes short finger sections 61–64 which, like the thumb section, are open ended. Here a plurality of adhesive patches 65–67 and 65a–67a may be used to assure retention in place. The positioning of the glove over the hand is as already described.

Figure 5:
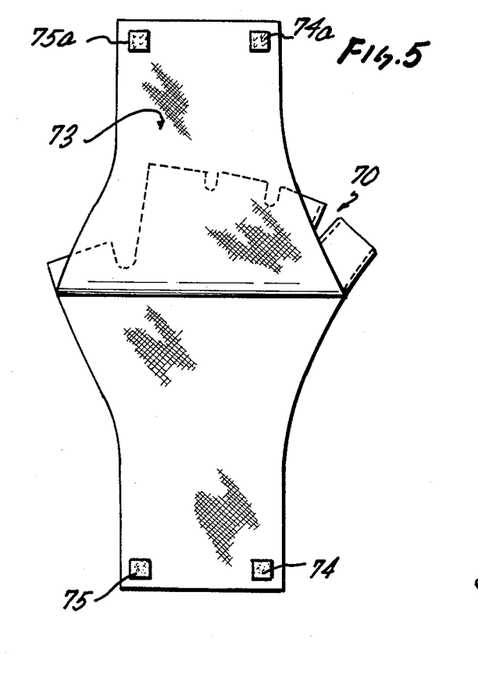
FIG. 5 is a plan view, again somewhat in perspective, of modified form of glove as illustrated in FIG. 4.

In another form of a short finger glove 70, illustrated in FIG. 5, again similar to that of FIG. 4, a full flap 73 may be used, again with adhesive patches 74–75 and 74a–75a, whose structure and function is as already described. This form of short finger glove may be used where the nature of the burn is such that it may be painful or difficult to insert the hand into the glove.

Figure 6:
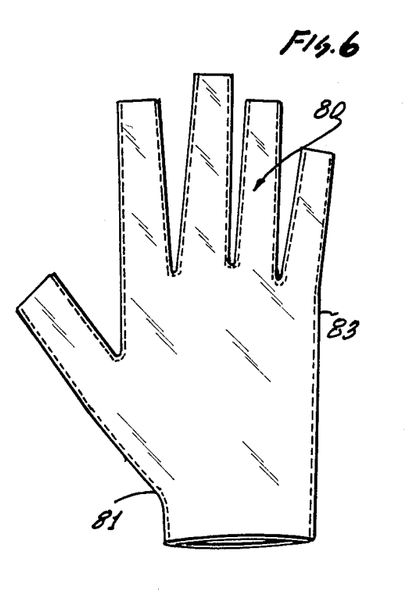
FIG. 6 is a plan view of a full glove-type product in accordance with the present invention.

A full fingered glove 80 is illustrated in FIG. 6 and is fabricated as already described with reference to FIG. 3, except that is entirely stitched along the sides 81, 83 and between the fingers, as shown. If desired a partial or full flap and adhesive patches may be used as described.

Figure 7:
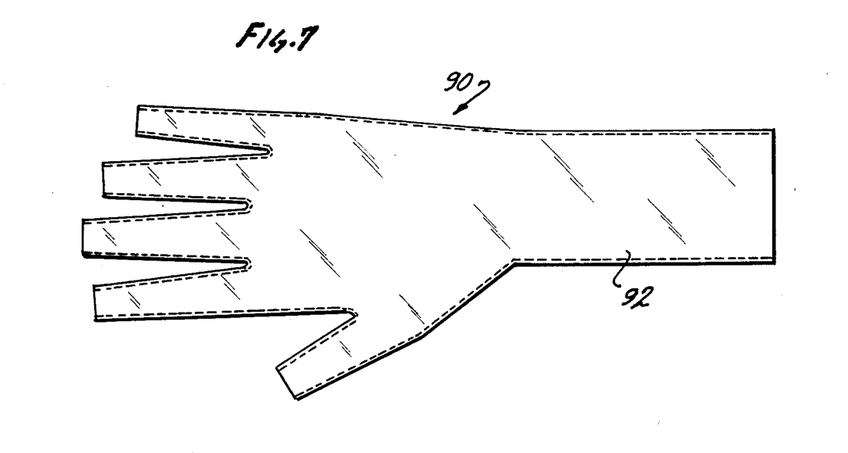
FIG. 7 is a plan view of an extended full glove-type of product in accordance with the present invention.

A modified form of full fingered glove 90 is shown in FIG. 7 in which the glove includes an extending portion 92 whose function is to provide coverage for the wrist area and a minor portion of the forearm. In all other respects, the glove 90 is of a similar structure of that illustrated in FIG. 6.

It apparent from the foregoing detailed description of the various products illustrated in FIGS. 1–7 that the stretch and compliant nature of the basic sheet product offer the ability to design or fabricate various products as they may be needed. These various products may be fabricated immediately before use or may be prefabricated. Thus, for example, a variety of different size gloves or glove-like products may be fabricated. So too, tubes and other shapes may be fabricated of a variety of lengths and diameters.

It is to be understood that the products above described may be used other than in the treatment of burns. Thus, for example, the products illustrated in FIGS. 3, 4, and 5 may be used to cover and to protect areas which have been grafted with autogenous skin to protect either the grafted skin site or the exposed wound, or both, from desiccation and infection from exogenous bacteria.

In any case, whether used as a burn dressing or for the protection of the skin surfaces which have been grafted or from which skin was taken for the graft, the good acute adherence of the product of the present invention is of significance in its use. The biologicals are used to enhance the early adherence to the wound site and the biofunctional property of the activated surface is important in achieving this acute adherence. In a preferred form, the acute adherence is achieved through the use of a gelatin material as the biological agent. Thus, the resulting product is a quite flexible material, stretchable by at least 50% in each direction, sufficiently thin to permit control of moisture vapor transport. By the use of a thin membrane, preferably of a silicone material as described, and a fabric backing of the type described, the product of this invention possesses unique qualities. In addition to the properties mentioned, the product of this invention is non-toxic, either acutely or systemically, is non-pyrogenic and non-antigenic, while demonstrating superior acute adherence. It is to be understood that acute adherence is a property different from being blood compatible and that the use of the present invention for the treatment of burns and the like requires acute adherence, as set forth in the data already reported.

Wounds tend to vary greatly with respect to the amount of exudate or transudate excreted. For optimal results, the wound site should be closed as occlusively as possible without allowing liquid to accumulate between the wound closure product, i.e., that of this invention, and the wound surface. If liquid accumulates subjacent the wound closure product, an ideal medium ("greenhouse effect") is created that allows rapid proliferation of endogenous bacteria, that is, the bacteria present in the wound. While the product of this invention allows passage of moisture vapor through the product at a fairly good rate, if the build up of exudate or transudate is faster than the transport, there may be a liquid build-up between the wound and the facing surface of the occlusive product.

Several different approaches may be used with the products of the present invention. For example, during the manufacturing process the formed composite is subjected to a punching operation during which small pinholes are placed in the composite. This operation is performed after the cure of the elastomer, such that the pinholes appear closed when the material is in the unstretched and relaxed condition. When the product is stretched, the pinholes open up. In another form, the small diameter holes are formed using specific sized needles as mandrels in the membrane layer with the elastomer in the uncured state. The membrane is cured with the mandrels in place. After curing, the mandrels are removed leaving pinholes in the membrane layer. The pinholes may be of various sizes depending upon need and design. The pinholes are fully open in the relaxed state of the product.

Although the products include small openings, as described, the resultant product is 98% or better occlusive. The products adhere to the wound site and allow elimination of the "dead space" between the product and the wound surface. In this way, proliferation of endogenous microorganisms, such as bacteria, fungi, virus or algae, may be reduced. Such pinholes also tend to promote higher water vapor transport, while allowing water or organic soluble antimicrobial agents to pass through the product to the wound itself. Thus, an outer dressing soaked with an appropriate agent may be applied over the outer surface of the product to permit passage of the agent directly to the site of the wound.

What is claimed is:

1. A material for use as a dressing for burns and the like comprising:
   a composite elastomeric substrate which includes a fabric facing and a backing of a thin polymeric material, said substrate including a surface adapted to be placed in overlying facing relation with the burn and the like,
   said composite elastomeric substrate being stretchable in all directions in an amount of at least 50% without permanent deformation, and being compliant,
   at least said surface of said substrate adapted to be placed in overlying relation with said burn and the like having functional groups selected from the group consisting of primary and secondary amino groups extending from at least a portion of the surface thereof,
   said amino groups having attached thereto a reactive group selected from the group consisting of aldehyde and cyanuric chloride groups,
   a biological having functional groups selected from the group consisting of primary and secondary amines and hydroxyl groups coupled to said surface by reaction between the primary or secondary amine, or hydroxyl group of said biological and one or more of the aldehyde and cyanuric chloride groups attached to said primary and secondary amino groups extending from at least a portion of said surface, and
   said biological imparting bio- and blood compatible characteristics to said portion of said surface.

2. A material as set forth in claim 1 wherein said composite elastomeric substrate has a water vapor transmission rate, as measured at 37 degrees C. for 24 hours, of at least 10 grams per hour per meter squared.

3. A material as set forth in claim 1 wherein the polymeric material has a thickness in the range of 0.0006 to 0.020 inches.

4. A material as set forth in claim 1 wherein said polymeric material has a thickness in the range of 0.0008 and 0.0012 inches.

5. A material as set forth in claim 1 wherein said polymeric material is selected from the group consisting of silicone rubber and elastomer polysiloxanes.

6. A material as set forth in claim 1 wherein said biological is selected from the group consisting of heparin, chrondroitin sulfate C, egg albumin, collagen, lysine, alanine, glutamic acid, glycine aspartic acid, glycylgylcine, human albumin, gelatin and lecithin.

7. A material as set forth in claim 1 wherein said composite elastomeric substrate is sufficiently thin to permit passage of water vapor therethrough and sufficiently thick to prevent liquid water from passing therethrough.

8. A material as set forth in claim 7 wherein said fabric is an 18/3 nylon mesh.

9. A material as set forth in claim 1 wherein said material is sterile.

10. A material as set forth in claim 1 wherein said biological is gelatin.

11. A material as set forth in claim 1 wherein said biological is aspartic acid.

12. A material for use as a dressing to be applied to the wound site of skin for treatment of burns and the like comprising;
   a sterilized composite sheet-like matrix material,
   said sheet-like matrix material including a mesh fabric facing which has an elongation in each direction of at least 50% and which forms the surface adapted to be placed in contact with the wound site of the burn and the like,
   a relatively thin polymeric membrane attached to said fabric such that the composite sheet-like matrix is elastic and stretchable in an amount greater that about 50% in all directions and is flexible and compliant,
   said polymeric membrane being sufficiently thin to permit passage of water vapor therethrough and sufficiently thick to prevent liquid water from passing therethrough,
   a biological chemically covalently coupled at least to that portion of said surface which constitutes the active surface and which is adapted to come into contact with the site of the burn and the like,
   said biological operating to increase the acute adherence of said active surface to the skin at the site of the burn and the like as compared to the same surface without said biological, and
   said material having the added properties of being non-antigenic, non-pyrogenic, and non-toxic both systematically and acutely.

13. A material as set forth in claim 12 wherein said biological is gelatin.

14. A material as set forth in claim 12 wherein said mesh fabric is a finely knitted biaxially stretchable fabric of 25 denier or less.

15. A material as set forth in claim 12 wherein the water vapor transmission rate, as measured at 37 degrees C. for 24 hours, is in the range of between 10 and 15 grams per meter squared.

16. A material as set forth in claim 12 in which said polymeric material is selected from the group consisting of silicon rubber and elastomeric polysiloxanes.

17. A material as set forth in claim 12 wherein said membrane has a thickness in the range of between 0.0008 and 0.0012 inches.

18. A material as set forth in claim 12 wheren said polymeric material is selected from the group consisting of silicone rubber and elastomeric polysiloxanes and wherein said membrane has a thickness in the range of 0.0008 and 0.0012 inches.

19. A material as set forth in claim 12 in which at least a portion of the sheet-like matrix material including adhesive means for adhering the sheet material to another surface.

20. A material as set forth in claim 19 wherein said material is in the form of a tubular member.

21. A material as set forth in claim 12 wherein said sheet-like member is in the form of a hollow member including edge portions having at least one open end, and
   at least a portion of the edge portions being secured together such that at least a portion of the interior portion of said hollow member is the active surface adapted to come into contact with the skin at the wound site.

22. A material as set forth in claim 21 wherein the other end thereof is closed.

23. A material as set forth in claim 21 wherein said hollow member includes at least one flap member to secure said hollow member in place.

24. A formed member for use as a dressing to be applied to the wound site of skin for treatment of burns and the like comprising;
   a sterilized composite formed structure composed of two spaced surface portions adapted to be spaced from each other,
   said surface portions being composed of a mesh fabric facing which has an elongation in each direction of at least 50% and which forms the surface adapted to be placed in contact with the wound site of the burn and the like,
   a relatively thin polymeric membrane attached to said fabric such that the surface portions are elastic and stretchable in an amount greater than about 50% in all directions and are flexible and compliant,
   said polymeric membrane being sufficiently thin to permit passage of water vapor therethrough and sufficiently thick to prevent liquid water from passing therethrough,
   a biological chemically covalently coupled at least to that portion of said surface which constitutes the active surface and which is adapted to come into contact with the site of the burn and the like,
   said biological operating to increase the acute adherence of said active surface to the skin at the site of the burn and the like as compared to the same surface without said biological, and
   said composite formed structure having the added properties of being non-antigenic, non-pyrogenic, and non-toxic both systemically and acutely.

25. A formed member as set forth in claim 24 wherein there are side portions and at least one open end portion,
   at least a segment of at least one of the side portions being joined together at least in part.

26. A formed member as set forth in claim 25 wherein said open end is a plurality of spaced openings.

27. A formed member as set forth in claim 26 wherein said plurality of spaced openings are finger openings.

28. A formed member as set forth in claim 27 wherein said finger openings are closed at their ends to form tubular finger openings.

29. A formed member as set forth in claim 25 wherein adhesive means are located at least along one of the side portions.

30. A formed member as set forth in claim 27 wherein said open portion is at one end thereof and wherein said formed member is at least partially closed at the other end thereof.

31. A formed member as set forth in claim 25 wherein said formed member is in the form of a glove having open ended finger portions.

32. A formed member as set forth in claim 25 wherein said formed member is a closed ended member in the form of a glove having closed ended finger elements.

* * * * *

UNITED STATES PATENT AND TRADEMARK OFFICE
CERTIFICATE OF CORRECTION

PATENT NO. : 4,725,279

DATED : February 16, 1988

INVENTOR(S) : E. Aubrey Woodroof

Page 1 of 2

It is certified that error appears in the above-identified patent and that said Letters Patent is hereby corrected as shown below:

Column 1, line 18, "there" should read --There---.

Column 2, line 5, "shelf like" should read --shelf life--; line 19, "product" should read --produce--; line 34, "othe" should read --other--; line 41, "Travis" should read --Tavis--.

Column 3, line 47, "the" should read --The--; line 58, "cloine" should read --choline--; line 68, "tansport" should read --transport--.

Column 4, line 39, "of secondary" should read --or secondary--; line 49, "the" should read --The--.

Column 5, line 34, "path" should read --patch--; line 59, "the" should read --The--.

Column 8, line 49, "setep" should read --step--.

Column 9, line 50, "disc" should read --discs--.

Column 10, line 47, "membranes" should read --membrane--.

Column 15, line 16, "3. No adherence" should read --1. No adherence--.

UNITED STATES PATENT AND TRADEMARK OFFICE
CERTIFICATE OF CORRECTION

PATENT NO. : 4,725,279

DATED : February 16, 1988

INVENTOR(S) : E. Aubrey Woodroof

It is certified that error appears in the above-identified patent and that said Letters Patent is hereby corrected as shown below:

Column 18, line 44, "that is" should read --that it is--.

Column 20, line 54, Claim 6, "glycine aspartic" should read --glycine, aspartic--.

Column 21, line 42, Claim 16, "silicon" should read --silicone--.

Column 21, line 52, Claim 19, "including" should read --includes--.

Signed and Sealed this

Twenty-seventh Day of September, 1988

Attest:

DONALD J. QUIGG

Attesting Officer     Commissioner of Patents and Trademarks